United States Patent [19]

Harrington et al.

[11] Patent Number: 4,892,814

[45] Date of Patent: Jan. 9, 1990

[54] METHOD FOR DISTINGUISHING CREUTZFELDT-JAKOB DISEASE FROM OTHER DEMENTIAS

[75] Inventors: Michael G. Harrington; Carl R. Merril, both of Rockville; David M. Asher, Chevy Chase; D. Carleton Gajdusek, Frederick, all of Md.

[73] Assignee: The United States of America as represented by the Department of Health and Human Services, Washington, D.C.

[21] Appl. No.: 67,420

[22] Filed: Jun. 22, 1987

[51] Int. Cl.[4] .............................................. C12Q 1/70
[52] U.S. Cl. ....................................... 435/5; 436/811; 424/2; 204/182.8
[58] Field of Search .................... 424/2; 436/149, 806, 436/811; 435/5; 530/412; 204/182.8

[56] References Cited

U.S. PATENT DOCUMENTS

| | | |
|---|---|---|
| 3,201,202 | 8/1965 | Searcy et al. |
| 3,540,850 | 11/1970 | Halpaap |
| 4,124,470 | 11/1978 | Dahms |
| 4,205,057 | 5/1980 | Whitaker |
| 4,416,998 | 11/1983 | Adams et al. |
| 4,468,466 | 8/1984 | Morrissey |
| 4,654,313 | 3/1987 | Hartman |

OTHER PUBLICATIONS

Annals. of Neur., vol. 13, No. 4 (1983), pp. 434–439.
Neurology, vol. 29 (1979), pp. 1610–1612.
Europ. Neurol., vol. 19 (1980), pp. 85–90.

*Primary Examiner*—Robert Benson
*Attorney, Agent, or Firm*—Browdy and Neimark

[57] ABSTRACT

A method for distinguishing Creutzfeldt-Jakob disease from other causes of human dementia by analyzing the cerebrospinal fluid of patients for proteins 130 and 131. The presence of these proteins indicates the presence of Creutzfeldt-Jakob disease.

3 Claims, No Drawings

METHOD FOR DISTINGUISHING CREUTZFELDT-JAKOB DISEASE FROM OTHER DEMENTIAS

FIELD OF THE INVENTION

The present invention relates to a method for diagnosing Creutzfeldt-Jakob disease.

BACKGROUND OF THE INVENTION

Creutzfeldt-Jakob disease is a fatal, transmissible form of dementia. Because of its infectious nature, diagnosis of this disease is most important.

The infectious agent is referred to as an "unconventional" virus or prion. There is no specific immune response to the infectious particle in the brain, serum, or cerebrospinal fluid of patients with this disease. Therefore, the usual diagnosis is an antemortem diagnosis which must be made by biopsy of affected brain tissue. The closest known technology for accurately diagnosing Creutzfeldt-Jakob disease is by directly examining abnormal brain tissue, either by light microscopy of a brain biopsy, identifying the presence or absence of a protein PrP 27–30 in extracts of brain biopsy tissue, or by a combination of the above, post-mortem. Detection of scrapie-associated fibrils by negative-stain electron microscopy and of "prion" proteins by electrophoresis of extracts from brain tissue provide additional information that is useful for diagnosis.

While it is possible to biopsy a live brain, this procedure is undertaken only with great reluctance for obvious reasons having to do with the adverse effects coupled with little potential benefit to the patient. A biopsy of brain tissue is not performed until late in the course of the disease because of the inherent risks of the procedure. On the other hand, cerebrospinal fluid can be readily obtained from patients. Unfortunately for the purpose of diagnosis, scrapie-associated fibrils and prion proteins have not yet been detected in spinal fluid.

Progress over the last decade in protein separation and staining has allowed the detection of approximately 300 proteins in the cerebrospinal fluid. Hartman, in U.S. Pat. No. 4,654,313, describes a radioimmunoassay for the determination of brain antigens or protein such as S-100, which is responsible for some neurological disorders.

Searcy et al., in U.S. Pat. No. 3,201,202, disclose a method for microquantitation of proteins in cerebrospinal fluid, but there is no disclosure of the purpose for which such proteins are quantitated.

Whitaker, in U.S. Pat. No. 4,205,057, disclose a method for isolating and using cerebrospinal fluid myelin encephalitogenic protein fragments as a disease indicator in multiple sclerosis.

Galvez et al., in Neurology 29: 1610–1612 (1970), disclose that the concentrations of IgA, IgG, and C3 in spinal fluid was increased over that of controls, suggesting a passage of IgG and C3 from the blood into spinal fluid.

Olsson, in European Neurology 19: 85–90 (1980), writes that no special abnormalities were found in cerebrospinal fluid from patients with Creutzfeldt-Jakob disease concerning cells, total protein content, or the concentrations of albumin and IgG.

Chu et al., in Annals of Neurology 13 (4): 434–439 (1983), discloses that no oligoclonal immunoglobulin G bands were detected in the cerebrospinal fluid of patients with Creutzfeldt-Jakob disease.

SUMMARY OF THE INVENTION

It is an object of the present invention to overcome the above-mentioned deficiencies in the prior art.

It is another object of the invention to provide a diagnostic test for Creutzfeldt-Jakob disease.

It is yet a further object of the present invention to provide a diagnostic test for Creutzfeldt-Jakob disease by detecting abnormal spinal fluid proteins.

According to the present invention, Creutzfeldt-Jakob disease is accurately diagnosed by the detection of proteins 130 and 131 in the spinal fluid of patients. This diagnosis can be made to differentiate Creutzfeldt-Jakob disease from other causes of dementia such as Alzheimer's disease, AIDS dementia, Huntington's disease, or the like, and without the adverse effects of brain biopsy. Additionally, the process of the present invention can be used to exclude the diagnosis of Creutzfeldt-Jakob disease in patients where spinal fluid proteins 130 and 131 are absent.

It has been found that spinal fluid proteins 130 and 131 are present in the spinal fluid of patients with Creutzfeldt-Jakob disease and in 50% of patients with Herpes simplex encephalitis. These proteins are absent in normal persons and in all other known types of dementia having symptoms similar to those of Creutzfeldt-Jakob disease. It is this absence of the abnormal proteins 130 and 131 in all other types of dementia that permits distinction of Creutzfeldt-Jakob disease from other causes of dementia.

Protein 130, Mr (relative molecular mass) 26,000 and pI (isoelectric point) 5.2; and protein 131, Mr 29,000 and pI 5.1, were present in all patients studied with Creutzfeldt-Jakob disease, and in 5 of 10 patients with herpes simplex encephalitis, but were absent from all of the other control groups.

Two other abnormal proteins that were identified in patients with Creutzfeldt-Jakob disease, Protein 127, Mr 40,000, pI 5.7; and Protein 128, Mr 40,000, pI 5.9; were also present in some patients with multiple sclerosis herpes simplex encephalitis, schizophrenia, Parkinsons's disease, or Guillain-Barre or Behcet's syndrome.

The identity and origin of these abnormal spinal fluid proteins are not yet known beyond identifying them by number and relative molecular weight and isoelectric point.

This invention has been published in the New England Journal of Medicine, 315: 279–283 (July 31, 1986) and the contents of this publication are incorporated herein by reference.

DETAILED DESCRIPTION OF THE INVENTION

Progress in protein separation and staining has allowed the detection of approximately 300 proteins in the cerebrospinal fluid. Normal polymorphic and age-related variations in the proteins have been reported.

Spinal fluid from 21 patients with Creutzfeldt-Jakob disease and from three patients with kuru was studied. The diagnosis of Creutzfeldt-Jakob disease was confirmed by histopathology as well as by experimental transmission to primates. Table I shows of the diseases studied, the number of patients with proteins 127 and 128, or 130 and 131, in their cerebrospinal fluid. The normal volunteers were screened for neurologic and psychiatric diseases.

TABLE 1.

Proteins 127 and 128, and 130 and 131 in the Cerebrospinal Fluid of Patients with Various Disorders.

| Diagnosis | Total No. of Patients | No. of Patients with The Proteins | |
|---|---|---|---|
| | | 127 and 128 | 130 and 131 |
| Normal volunteers | 100 | 0 | 0 |
| Creutzfeldt-Jakob disease | 21 | 14 | 21 |
| Kuru | 3 | 0 | 0 |
| Alzheimer's disease | 37 | 0 | 0 |
| Parkinsonism-dementia complex of Guam | 18 | 0 | 0 |
| AIDS dementia | 3 | 0 | 0 |
| Huntington's disease | 26 | 0 | 0 |
| Multiinfarct dementia | 3 | 0 | 0 |
| Cerebral infarction | 6 | 0 | 0 |
| Progressive supranuclear palsy | 5 | 0 | 0 |
| Herpes simplex encephalitis | 10 | 9 | 5 |
| Schizophrenia | 54 | 17 | 0 |
| Parkinson's disease | 26 | 3 | 0 |
| Multiple sclerosis | 130 | 17 | 0 |
| Guillain-Barre syndrome | 4 | 4 | 0 |
| Behcet's disease | 1 | 1 | 0 |
| Subacute sclerosing panencephalitis | 7 | 0 | 0 |
| Encephalitis | | | |
| Cytomegalovirus | 1 | 0 | 0 |
| Mumps | 1 | 0 | 0 |
| Varicella | 1 | 0 | 0 |
| Japanese B | 2 | 0 | 0 |
| St. Louis | 2 | 0 | 0 |
| California | 6 | 0 | 0 |
| Tuberculous meningitis | 3 | 0 | 0 |
| Neurosyphilis | 3 | 0 | 0 |
| Cerebral toxoplasmosis | 1 | 0 | 0 |
| Headache | 4 | 0 | 0 |
| Amyotrophic lateral sclerosis | 6 | 0 | 0 |
| Cerebellar lymphoma | 1 | 0 | 0 |
| Shy-Drager syndrome | 8 | 0 | 0 |
| Idiopathic orthostatic hypotension | 3 | 0 | 0 |
| Korsakoff's psychosis | 6 | 0 | 0 |
| Essential tremor | 5 | 0 | 0 |
| Dystonia | 3 | 0 | 0 |
| Manic-depressive psychosis | 26 | 0 | 0 |
| Unknown | 5 | 0 | 0 |
| Total | 541 | 65 | 26 |

The samples of cerebrospinal fluid were obtained form the patients and stored at −70° C. without preservative before use. Volumes of spinal fluid samples containing 40 micrograms of total protein were denatured with detergents, mercaptoethanol, and urea. The proteins were then separated with two-dimensional electrophoresis. The first dimension, isoeletric focusing, used a 4:1 mixture of pH 5 to 7 and pH 3 to 10 ampholytes. The second dimension used polyacrylamide gel electrophoresis in the presence of sodium dodecyl sulfate.

The proteins were detected by silver staining. The staining is based on the specific reduction of silver to its metallic form in the presence of polypeptides. Gels are incubated in a solution containing methanol and acetic acid, and pretreated with dithiothreitol before adding silver nitrate. The silver is then selectively reduced in the presence of formaldehyde, and sodium carbonate. Changes were observed by both direct visual scanning and computer-assisted densitometry of gels for assessment of alterations from the normal spinal fluid pattern.

After the abnormal proteins were found in the cerebrospinal fluid from the patients with Creutzfeldt-Jakob disease, the relative molecular mass (Mr) values of those proteins were obtained by comparisons with purified standards obtained from Pharmacia subjected to coelectrophoresis. The relative isoelectric point (pI) values were determined by comparison with the pH gradient observed in an isoelectric focusing gel that was subjected to coelectrophoresis, cut into 2 mm slices, and solubilized in deionized water for pH measurement.

Two experiments were performed to assess whether the four additional proteins arose from degradation or post-translational modification of normal spinal fluid proteins.

First, because many cerebrospinal fluid proteins exist as multiple sialated derivatives, normal spinal fluid was incubated at 37° C. for 1 to 24 hours with neuraminidase, 0.5 to 50 units per milliliter. In the second experiment, the spinal fluid was incubated at 25° C. in the absence of proteolytic inhibitors for up to three months to assess whether protease activity in the cerebrospinal fluid would produce abnormal proteins. Spinal fluid samples from both experiments were then subjected to electrophoresis and silver staining and analyzed as described above.

The initial survey for abnormal proteins involved fluids from patients for whom the diagnosis was known. Each patient's fluid was accompanied by a control spinal fluid sample that had been stored under the same conditions in the contributing laboratory. A study was then conducted to assess the appearance of abnormal proteins as a means of distinguishing Creutzfeldt-Jakob disease, Alzheimer's disease, Huntington's disease, multiinfarct dementia, parkinsonism dementia of Guam, and the specific dementia associated with the acquired immune deficiency syndrome (AIDS). Proteins were analyzed, and the presence or absence of abnormal proteins was recorded.

The electrotransfer of proteins separated by two-dimensional electrophoresis to nitrocellulose was performed. The nitrocellulose transfers were incubated with primary rabbit antibodies and stained with avidin-biotin-peroxidase, as described by the manufacturers, Vekastain. Goat antirabbit IgG was used as the secondary IgG, and 4-chloro-1-naphthol or 3,3'-diaminobenzidine tetrahydrochloride was used as peroxidase substrate. The primary antibodies included polyclonal herpes simplex virus antibody, polyclonal antiserum against PrP 27–30 scrapie-associated protein, polyclonal anti-kappa and anti-lambda light chain antibodies, and polyclonal anti-J-chain antiserum. The antibodies were all demonstrated to react positively against their appropriate antigens under the same conditions employed with the test samples.

Changes in the spinal fluid proteins in all patients were identified by comparison with the proteins in the 100 normal persons. Four abnormal proteins, which were designated 127, 128, 130, and 131, were consistently observed in the spinal fluid from the 21 patient with Creutzfeldt-Jakob disease. These proteins were not found in the cerebrospinal fluid of 91 percent of the patients with other neurological disorders, including the three patients with kuru. Proteins 127 and 128 both had an Mr of 40,000, and their pI values were 5.7 and 5.9, respectively. Protein 130 had an Mr of 26,000 and a pI of 5.2, and protein 131 had an Mr of 29,000 and a pI of 5.1.

The experiments as described above were conducted to assess whether the four abnormal proteins arose from degradation or post-translational modification of normal spinal fluid proteins. During these experiments, no proteins migrated to the positions occupied by proteins 127, 128, 130, or 131.

Proteins 130 and 131 always appeared together and were present in all 21 samples from patients with Creutzfeldt-Jakob disease. After silver staining, proteins 130 and 131 had a bluish color, which is typical of some lipoproteins. Spinal fluid from an additional 520 patients with a variety of neurological diseases and from normal persons was examined for proteins 130 and 131 (cf. Table I), and these proteins were found in only 50 percent of patients with herpes simplex encephalitis.

A blinded study was performed to determine whether the presence of proteins 130 and 131 in spinal fluid could be used to distinguish Creutzfeldt-Jakob disease from other illnesses in which dementia occurs. All of the cases of Creutzfeldt-Jakob disease were correctly identified by the presence of proteins 130 and 131. There were no false positives.

Proteins 127 and 128 also always appeared together. Although these proteins were never present in sample from normal persons, they were detected in 67 percent of samples from patients with Creutzfeldt-Jakob disease, as well as in samples from patients with schizophrenia (31 percent), herpes simplex encephalitis (90 percent), multiple sclerosis (13 percent), Parkinson's disease (12 percent), or Guillain-Barre or Behcet's syndrome (all cases studied). This nonspecificity probably reflects a protein response to a common pathologic process in all of the patients.

Scrapie is a disorder of sheep that is similar to Creutzfeldt-Jakob disease in humans. A protein complex described in scrapie, (PrP 27-30), which is purified from scrapie-infected hamster brains, has been used an an antigen for the production of polyclonal antiserums. The antisera are not only specific for scrapie-infected brains, but also react with proteins of similar electrophoretic mobility that appear in the brains of patients with Creutzfeldt-Jakob disease. The relative mass of the cerebrospinal fluid proteins 130 and 131 is similar to that of the PrP 27-30 complex, but the complex has a much more basic pI. An antiserum to PrP 27-30 was used to probe Western blots containing proteins 127, 128, 130, and 131. Since no reactivity was detected, proteins 127, 128, 130, and 131 appear to be different from the scrapie PrP proteins.

The proteins were determined to be unrelated to the structural components of herpes simplex virus type 1, kappa and lambda light chains, or the J-chain protein by a variety of tests. The proteins were probed with a polyclonal antibody raised against cells infected with herpes simplex virus type 1, and probing with monoclonal antibodies against kappa and lambda light-chain and J-chain proteins. The antibody to herpes simplex virus type 1 was chosen because all four abnormal proteins were also found in the spinal fluid from some of the patients with herpes simplex encephalitis. The latter two proteins were considered because the pI and Mr of proteins 130 and 131 are similar to those of the known light-chain and J-chain proteins.

There are two plausible interpretations for the association between the presence of the four abnormal proteins in patients with Creutzfeldt-Jakob disease and the presence of these proteins in patients with other diseases. First, the proteins may all result from a pathophysiological process common to several degenerative neurologic diseases. None of the four proteins was detected in the samples of spinal fluid from the patients with kuru, even though kuru is a form of Creutzfeldt-Jakob disease that is spread by the cannibalistic rituals of the Fore people. The absence of proteins 130 and 131, which were found in all of the patients with Creutzfeldt-Jakob disease, from the spinal fluid of the patients with kuru that were studied, would indicate that kuru and Creutzfeldt-Jakob disease are different disorders.

An alternative explanation for the appearance of the four proteins is that they are associated with latent herpes simplex virus infection, since 50 percent of the patients with herpes simplex encephalitis had all four abnormal proteins and 90 percent of those patients had proteins 127 and 128. Since herpes simplex virus is frequently present (but clinically dormant) in normal persons, it is conceivable that Creutzfeldt-Jakob disease (and the other diseases in which these proteins appear) triggered a latent herpes simplex virus infection, which then produced the proteins that were detected in the spinal fluid. The negative results of the immunoblot assays with polyclonal antibody to herpes simplex virus type 1 weaken this interpretation.

Although the origin of proteins 130 and 131 is unknown, the apparent specificity of these proteins in Creutzfeldt-Jakob disease and herpes simplex encephalitis indicate that their presence in spinal fluid may be of considerable help in differentiating Creutzfeldt-Jakob disease from other common types of human dementia, particularly Alzheimer's disease. Although the finding of proteins 130 and 131 does not permit differentiation of Creutzfeldt-Jakob disease from herpes simplex encephalitis, it is generally not difficult to distinguish these two diseases clinically. Although the presence of proteins 127 and 128 in several disease states, including Creutzfeldt-Jakob disease, is nonspecific, their identification may be of diagnostic value in distinguishing between organic and functional central nervous system diseases.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

What is claimed is:

1. A method for distinguishing Creutzfeldt-Jakob disease from other causes of human dementia wherein it has been clinically determined that the patient does not suffer from herpes simplex encephalitis comprising analyzing the cerebrospinal fluid of a patient for proteins 130 and 131, the presence of proteins 130 and 131 in the cerebrospinal fluid indicating the presence of Creutzfeldt-Jakob disease.

2. The method of claim 1 wherein the proteins are separated from the cerebrospinal fluid by electrophoresis.

3. The method of claim 2 wherein the proteins are detected with silver staining.

* * * * *